United States Patent
Hutchenson et al.

(10) Patent No.: US 7,141,682 B2
(45) Date of Patent: *Nov. 28, 2006

(54) LIQUID PHASE SYNTHESIS OF METHYLENE LACTONES USING OXNITRIDE CATALYST

(75) Inventors: Keith W. Hutchenson, Lincoln University, PA (US); Kostantinos Kourtakis, Media, PA (US); Leo Ernest Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/168,626

(22) Filed: Jun. 28, 2005

(65) Prior Publication Data

US 2006/0025604 A1    Feb. 2, 2006

Related U.S. Application Data

(60) Provisional application No. 60/591,520, filed on Jul. 27, 2004.

(51) Int. Cl.
| | |
|---|---|
| *C07D 307/02* | (2006.01) |
| *C07D 407/00* | (2006.01) |
| *C07D 305/12* | (2006.01) |
| *C07D 307/26* | (2006.01) |
| *C07D 307/34* | (2006.01) |

(52) U.S. Cl. .................................. 549/295; 549/326
(58) Field of Classification Search ................ 549/295, 549/326

See application file for complete search history.

(56) References Cited

U.S. PATENT DOCUMENTS

| 6,232,474 B1 | 5/2001 | Brandenburg et al. |
| 2006/0025606 A1* | 2/2006 | Hutchenson et al. ........ 549/263 |
| 2006/0025609 A1* | 2/2006 | Hutchenson et al. ........ 549/263 |

FOREIGN PATENT DOCUMENTS

| JP | 10298172 | * 11/1998 |
| WO | WO9952628 | 10/1999 |
| WO | WO 03/053913 | 7/2003 |

OTHER PUBLICATIONS

M. J. Climent et al., Catalysis Letter, 59 (1999) 33-38.
P. Grange et al., Applied Catalysis A: General, 114 (1994) L191-L196.
P. Grange et al., Applied Catalysis A: General, 137 (1996) 9-23.
Journal of Chemical Physics (2003) 119, (18) 9765-9770.

* cited by examiner

*Primary Examiner*—Thomas McKenzie
*Assistant Examiner*—Niloofar Rahmani

(57) ABSTRACT

Process for converting certain lactones to their alpha-methylene derivatives in the liquid phase using oxynitride catalysts or composite catalysts incorporating dithium, sodium, potassium, rubidium, cesium, magnesium, calcium, strontium, or barium or combinations thereof.

5 Claims, No Drawings

US 7,141,682 B2

LIQUID PHASE SYNTHESIS OF METHYLENE LACTONES USING OXNITRIDE CATALYST

CROSS-REFERENCE TO RELATED APPLICATION

This application claims priority under 35 U.S.C. §119 from U.S. Provisional Application Ser. No. 60/591,520, filed Jul. 27, 2004.

FIELD OF INVENTION

The invention pertains to a method of producing unsubstituted and substituted alpha-methylene lactones by a liquid phase reaction of starting lactones with formaldehyde in the presence of an oxynitride catalyst or a oxynitride composite catalyst.

BACKGROUND

Alpha-methylene-gamma-butyrolactone and methyl alpha-methylene-gamma-butyrolactone are useful monomers in the preparation of both homopolymers and copolymers. In addition, the alpha-methylene-gamma-butyrolactone group is an important structural feature of many sesquiterpenes of biological importance.

U.S. Pat. No. 6,232,474 B1 describes a method for converting certain starting lactones to alpha-methylenelactones using a homogeneous or heterogeneous so-called basic catalyst that can be selected from the metal oxides, hydroxides, carbonates and phosphates, any of which may be supported or unsupported. The preferred reaction is the conversion of gamma-butyrolactone to alpha-methylene-gamma-butyrolactone. The basic catalyst may include additives and promoters to enhance catalyst efficiency. The method involves a reaction between the starting lactone and formaldehyde and may be carried out in a batch mode, optionally using an organic solvent and a phase transfer agent. The method is carried out at a temperature of at least 70° C. and a pressure less than or equal to 2000 psi (13.7 MPa).

The prior art in this area involves the use of supported catalysts on silica, which are known to be hydrothermally unstable (see for instance, WO9952628A1). Under reaction conditions, or after repeated regeneration cycles, a hydrothermally unstable material will show catalytic performance that will deteriorate with time.

Aluminum phosphorous oxynitrides are a relatively new category of materials, which may have unique properties for base catalyzed chemistry. These materials are believed to have adjustable acid/base properties. These phosphorus oxynitrides, which were first described by M. J. Climent (M. J. Climent et al., Catalysis Letter, 59 (1999)33–38; P. Grange et al., Applied Catalysis A: General 114 (1994) L191–L196; P. L. Grange et al., Applied Catalysis A: General, 137 (1996) 9–23) have been shown to be active for various base catalyzed condensation reactions (e.g., arylsulfones with substituted benzaldehydes). Structural information is not available. However, depending on the nitridation temperature and other conditions, and therefore degree of incorporation of nitrogen into the structure of these materials, it was shown that the relative proportion of acidic and basic sites in the catalyst could be adjusted. However, the use of these materials for lactone conversion has not been described, either as the oxynitrides or as composite catalysts in which various Group I and/or Group II elements are incorporated into the oxynitride.

Although a phosphorus oxynitride system might be expected to possess a significant advantage in hydrothermal stability compared to conventional silica catalysts, the catalytic activity of such a material for lactone conversion reactions cannot be predicted because of the unpredictable nature of catalysis in general.

It would be advantageous to have a catalyst that is hydrothermally stable at high temperatures and whose activity does not decay with time on stream (TOS) or after several high temperature oxidizing regenerations.

SUMMARY OF THE INVENTION

This invention relates to the discovery that the phosphorus oxynitrides and oxynitride composites (as defined below) are surprisingly active for lactone conversion chemistry, with the advantage that they should possess superior hydrothermal stability compared to prior art supported silica catalysts.

In its first aspect, the present invention is a process for preparing a reaction product comprising an alpha-methylene lactone of the Formula II, said process comprising reacting a lactone of the Formula I with formaldehyde

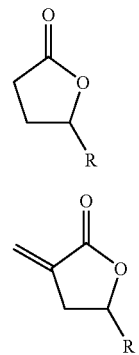

wherein R is selected from the group consisting of hydrogen, methyl, ethyl, and straight or branched $C_3$–$C_5$ alkyl; at a temperature in the range of from about 100° C. to 300° C. and a pressure in the range of 0.34 MPa to 13.7 MPa in the presence of a catalyst of the nominal formula

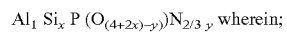

$Al_1 Si_x P (O_{(4+2x)-y})N_{2/3\,y}$ wherein;

x=0 to 1, and
y=0.001 to 2.

In its second aspect the invention involves the same reaction wherein the oxynitride catalyst is made by (is obtainable by) a process comprising:

(a) combining $AlCl_3$ or aluminum alkoxides containing 1–20 carbon atoms with water;
(b) adding $H_3PO_4$ to the product of step (a);
(c) optionally adding silicon alkoxide to the product of step (b);
(d) adding $NH_4OH$ to the product of step (b), or to the product of step (c) if step (c) is performed;
(e) drying the product of step (d);
(f) optionally washing the product of step (e); and
(g) heating the product of step (e) or (f) in $NH_3$.

In its third aspect, the invention involves the same reaction wherein the catalyst is a composite catalyst that is a reaction composite of the oxynitride catalyst and an element selected from Group I and/or Group II of the Periodic Table, made by (obtainable by) a process comprising:

(a) contacting (i) the oxynitride catalyst with (ii) a solution comprising a solvent and a compound of at least one element selected from the group consisting of lithium, sodium, potassium, rubidium, cesium, magnesium, calcium, strontium and barium;

(b) drying the product of step (a) to remove at least a portion of said solvent;

(c) heating the product of step (b) to a temperature in the range of 350° C. to 550° C. to produce a catalyst precursor; and (d) flushing at a preselected flow rate an oxygen-containing gas over said catalyst precursor either during step (c), or after step (c) while the temperature is still in the range of 350° C. to 550° C. to produce the composite catalyst in which the at least one element is present in said composite catalyst in an amount from about 0.1% to about 40% by weight of the combined weight of the oxynitride catalyst and the element.

Catalysts used in the present invention might be expected to confer an advantage over silica-based catalysts in terms of hydrothermal stability of the present phosphorus oxynitrides on the theory that any enhancement of the lattice energy of a solid will yield a thermally and hydrothermally stable material. In terms of their fundamental inorganic properties, phosphate systems are more ionic compared to the silicon oxides by virtue of the phosphate group relative to the oxygen anion. This will in turn strengthen the interactions between the positively and negatively charged species in the lattice, stabilizing the structure. This explanation has been applied to the incorporation of $La^{3+}$ in zeolitic structure (Yang, Gang; Wang, Yan; Zhou, Danhong; Zhuang, Jianqin; Liu, Xianchun; Han, Xiuwen; Bao, Xinhe, "On configuration of exchanged La3+ on ZSM-5: a theoretical approach to the improvement in hydrothermal stability of La-modified ZSM-5 zeolite" Journal of Chemical Physics (2003), 119 (18), 9765–9770).

DETAILED DESCRIPTION OF THE INVENTION

The following terms generally are abbreviated as follows:
alpha-methylene-gamma-butyrolactone is abbreviated MBL;
gamma-butyrolactone is abbreviated GBL;
gamma-valerolactone is abbreviated GVL;
alpha-methylene-gamma-valerolactone is abbreviated MVL;
gamma-methyl alpha methylene gamma butyrolactone is abbreviated MeMBL;
mass spectroscopy is abbreviated MS;
gas chromatography is abbreviated GC; and
standard cubic centimeters is abbreviated sccm.

The process of the present invention concerns a liquid phase methylenation of lactones of Formula I to yield alpha-methylene lactones of Formula II.

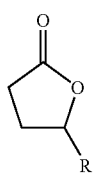

I

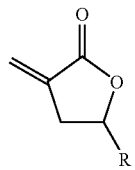

II

Specifically, lactone of Formula I is reacted with formaldehyde to give a reaction product comprising alpha methylene lactones of Formula II. The substituent —R group is selected from the group consisting of hydrogen, methyl, ethyl, and straight or branched $C_3$–$C_5$ alkyl.

In a preferred embodiment the lactone of Formula I is gamma-valerolactone (R is $CH_3$) and the alpha-methylene lactone of Formula II is alpha-methylene-gamma-valerolactone.

The process of the present invention is carried out in the liquid phase, at a temperature in the range of from about 100° C. to about 300° C. A temperature in the range of from about 150° C. to about 250° C. is preferred. A temperature in the range of from about 200° C. to about 225° C. is most preferred.

The reaction can be carried out at pressures ranging from about 0.34 MPa to about 13.7 MPa, with a preferred range of from about 0.68 MPa to about 6.85 MPa. Holdup time and temperature can be selected to achieve desired conversions and selectivities.

The formaldehyde may be supplied to the reaction in the form of an aqueous solution (formalin), a hemiacetal of an alcohol, a low molecular weight polyformaldehyde or formaldehyde trimer (trioxane). Paraformaldehyde is preferred. The use of the trimers and oligomers, however, reduces the need to remove water from the process. Anhydrous formaldehyde can also be used. Hemiacetals work effectively, but require separate steps to release the formaldehyde from the alcohol and to recover and recycle the alcohol.

The oxynitride catalyst used in the present invention is a mixed phase material that may be represented by the nominal formula:

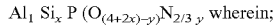

$Al_1 Si_x P (O_{(4+2x)-y} N_{2/3\,y}$, wherein;

x=0 to 1, and
y=0.001 to 2.

The catalyst can be made by a process (is obtainable by a process) that comprises the steps of:

(a) combining $AlCl_3$ or aluminum alkoxides containing 1–20 carbon atoms with water;

(b) adding $H_3PO_4$ to the product of step (a);

(c) optionally adding silicon alkoxide to the product of step (b);

(d) adding $NH_4OH$ to the product of step (b), or to the product of step (c) if step (c) is performed;

(e) drying the product of step (d);

(f) optionally washing the product of step (e); and (g) heating the product of step (e) or (f) in $NH_3$.

The relative number of acid and base sites on the catalyst can be adjusted by varying the time and temperature of step (g). The nitridation step in $NH_3$ introduces nitrogen into the lattice of the oxide, presumably through direct substitution of oxygen. This nitride formation (nominal $N^{3-}$) introduces basic sites on the catalyst surface.

The alkoxides of aluminum used in steps (a) or of silicon in step (c) may include any alkoxide that contains from 1 to 20 carbon atoms and preferably contains 1 to 5 carbon atoms in the alkoxide group. $C_1$–$C_4$ alkoxides such as aluminum n-butoxide and aluminum isopropoxide may be used. Tetraethylorthosilicate is an example of a silicon alkoxide for step (c), although other alkoxides containing silicon can be used such as tetremethyoxysiloxane.

Commercially available alkoxides can be used. However, other routes can prepare inorganic alkoxides. Examples include alkoxides prepared by the direct reaction of zero valent metals with alcohols in the presence of a catalyst. Many alkoxides can be formed by reaction of metal halides with alcohols. Alkoxy derivatives can be synthesized by the reaction of the alkoxide with alcohol in a ligand interchange reaction. Direct reactions of metal dialkylamides with alcohol also form alkoxide derivatives. Additional examples are disclosed in "Metal Alkoxides" by D. C. Bradley et al., Academic Press, (1978).

For step (a), aluminum chloride is preferred. For step (c), tetraethylorthosilicate is preferred.

For step (e), the drying may be conducted in air or an inert gas such as nitrogen, helium or argon.

In another embodiment, the oxynitride catalyst may be used to form a composite catalyst that is a reaction product of a catalytic Group I and/or Group II element of the Periodic Table and the oxynitride catalyst. Such catalysts can be made by (are obtainable by) a process that comprises the steps of:

(a) contacting (i) the oxynitride catalyst with (ii) a solution comprising a solvent and a compound of at least one element selected from the group consisting of lithium, sodium, potassium, rubidium, cesium, magnesium, calcium, strontium and barium;

(b) drying the product of step (a) to remove at least a portion of said solvent;

(c) heating the product of step (b) to a temperature in the range of 350° C. to 550° C. to produce a catalyst precursor; and (d) flushing at a preselected flow rate an oxygen-containing gas over said catalyst precursor either during step (c), or after step (c) while the temperature is still in the range of 350° C. to 550° C. to produce the composite catalyst, in which the at least one element is present in said composite catalyst in an amount from about 0.1% to about 40% by weight of the combined weight of the oxynitride catalyst and the element.

The inclusion of a Group I and/or Group II element into the oxynitride catalyst may cause a shift in the relative number of acid and base sites.

Organic compounds such as the carboxylates, such as acetate, propionate, butyrate, and 2-ethylhexanoate of a catalytic element selected from the group consisting of lithium, sodium, potassium, rubidium, cesium, magnesium, calcium, strontium and barium are dissolved in aqueous or non-aqueous solvent and contacted with the oxynitride catalyst. Organic compounds containing acetates are preferred. Other organic anions such as acetylacetonates can be used. The amount of organic compound should be chosen to provide to the final composite catalyst from 0.1 wt % to 40 wt % of the element relative to the combined weight of the oxynitride catalyst plus the element (as opposed to the compound of which the element is a part). The resulting material is allowed to dry, preferably in a nitrogen environment for an extended time. The purpose of the drying is to remove at least a portion of the solvent in which the organic compound is dissolved.

Organic compounds such as the alkoxides can also be used. Organic alkoxides of an element selected from the group consisting of lithium, sodium, potassium, rubidium, cesium, magnesium, calcium, strontium, and barium can contain from one to 20 carbon atoms and preferably 1 to 5 carbon atoms in the alkoxide group. The organic alkoxide should be soluble in the solvent. Most alkoxides can be dissolved in non-aqueous solutions such as ethanol, propanol, or isopropyl alcohol. Subsequent methods for introducing the element and drying are the same.

The dried material is then heated (for example in an alumina boat placed in a tube furnace) at an ambient temperature of 350° C. to 550° C. (The temperature of the catalyst material may be somewhat higher because of exothermic reactions taking place on the material.) A temperature between 450° C. and 550° C. is preferred. Either during the heating or subsequent to it, but at the same temperature, the material is flushed with an oxygen-containing gas (e.g. air), which is believed to burn off organic residues formed during the heating step. In a tube furnace, an airflow rate of at least 110 cc/min in a 3 cm diameter tube furnace, which corresponds to a linear velocity of 15.6 cm/min was found to be acceptable. Use of sufficiently high airflow rates are preferred to produce a high surface area material. In a tube furnace, the material can be heated at a rate of 5° C./min to 120° C., and can be exposed to this temperature for 4 hours. It can be heated subsequently at a rate of 5° C./min to approximately 450° C. and held at this temperature for 16 hours. Other equipment can be used to perform the heating step. Such equipment includes fluidized bed and rotary calcination equipment.

Heating can be accomplished in air or in a combination of an inert gas such as nitrogen, argon, or krypton for parts of the cycle, followed by air. An initial drying step at 120° C. in nitrogen, another inert gas, or air is preferred for a period of 30 minutes to 24 hours. Following this drying step, the catalyst can be heated in air or nitrogen to a temperature of 350° C. to 550° C. For acetate precursors, 450° C. to 550° C. is required. Heating times can range from 30 minutes to 48 hours. The final heating step preferably is performed in air for at least 30 minutes.

In some cases, reaction conditions may result in a decrease of catalyst efficiency. In these situations it may be useful to periodically reactivate the catalyst. For example, contacting the present catalysts, when activity drops below an acceptable level, with oxygen at elevated temperatures has the effect of reactivating the catalyst. Contact temperatures with oxygen may range from about 225° C. to about 500° C., with temperatures of about 250° C. to about 425° C. being preferred.

Thermal and hydrothermal stability are required for the catalyst to withstand one or repeated regeneration cycles without permanently degrading catalyst performance.

Selectivities and yields of product may be influenced by the total holdup time with the catalyst and reaction temperature.

The reaction may be done neat or in the presence of a non-reacting solvent such as toluene, xylenes and dioxane.

Separation and/or purification of the desired products, including MBL or MeMBL, from unreacted starting lactone and/or reaction byproducts may be performed by processes known in the art. A particularly suitable method to recover the desired product is to polymerize MBL in GBL solution, or MeMBL in GVL solution, using standard free-radical polymerization, isolate the polymer by precipitation, and then thermally depolymerize back to MBL or MeMBL, as the case may be, by heating under vacuum. Finally, MBL can be separated from GBL by melt crystallization. Another effective method is liquid-liquid extraction.

Non-limiting reactors suitable for the process of the instant invention include autoclaves, trickle bed, fixed bed and pipeline reactors. The process can be run in either batch or continuous mode as described, for example, in H. Scott Fogler, *Elements of Chemical Reaction Engineering*, 2$^{nd}$ Edition, Prentice-Hall Inc, Calif., 1992.

COMPARATIVE EXAMPLES

Comparative Catalyst 1: Approximately 12 wt % Rb on Aluminum Phosphorus Oxide 115.88 g of aluminum trichloride hexahydrate (Aldrich, 23,707-8) was addd to 180 g of water and 32 ml of 86% phosphoric cid (JT Baker). The material was stirred well. 150 ml of 20–30% ammonium hydroxide (EM sciences) was slowly added to this mixture until it reached a pH of 5.1. The material was allowed to age in a nitrogen atmosphere for 12 hours. It was washed with isopropyl alcohol.

After drying, about 9.5 g of this material was used, assuming about 36.5 wt % residual solvent in this gel. 2.54 g of rubidium acetate (Alfa Aesar, 12890) was dissolved in 5 g of water. About 3 g of this solution was impregnated into the gel.

After drying in nitrogen, the material was loaded into an alumina boat and heated in a 3 cm (outside diameter) tube furnace. In this tube furnace, an airflow rate of at least 110 cc/min was used, which corresponds to a linear velocity of 15.6 cm/sec.

EXAMPLES OF THE INVENTION

Catalyst 1: Approximately 15.5 wt % Rb supported on ($Al_1 Si_x P (O_{(4+2x)-y)})N_{2/3\ y}$, x=0, y is approximately 0.39)

115.88 g (0.86 moles) of aluminum trichloride (Alfa Aesar, 8848) was hydrolyzed with 322 g of water and left in solution overnight. One half of this hydrolyzed solution was used. 28.6 ml of 86% $H_3PO_4$ (JT Baker) was stirred into this half of the solution and was stirred well. After adding 116 ml of ammonium hydroxide (20–30%, EM Science) the material turned into a thick gel. After aging overnight, the material was dispersed with 300 ml of isopropyl alcohol (EM Sciences, Omnisolve) and filtered and washed with two 100 ml portions of isopropyl alcohol.

The material was nitrided by placing the material in a tube furnace and heated in anhydrous ammonia. 7.486 g of the solid described above was loaded in an alumina boat, which was placed into a tube furnace and purged in $N_2$ for 40 minutes (100 sccm $N_2$). The sample was heated to 70° C. in nitrogen and allowed to soak for 1 hour and then to 500° C. in $N_2$ for 4 hours. The $N_2$ was replaced with 100 sccm anhydrous $NH_3$ and the powder was heated to 800° C., and allowed to soak at that temperature (in $NH_3$) for 8 hours. After replacing the $NH_3$ with 100 sccm $N_2$, the sample was cooled to 500° C. and held at that temperature for 12 hours. The cycle was repeated: the $N_2$ was replaced with 100 sccm $NH_3$ and the powder was heated to 800° C. under $NH_3$ for 8 hours, for a total heating time in $NH_3$ of 16 hours at 800° C. After switching the gas stream to 200 sccm $N_2$, the sample was allowed to slowly cool to room temperature. The final product was analyzed for nitrogen content by Micro-Analysis Inc., Wilmington Del. In this analysis, a Perkin Elmer 2400 CHN analyzer was used which uses a combustion method to convert the sample elements to simple gases ($CO_2$, $H_2O$, and $N_2$). The sample was first oxidized in a pure oxygen environment; the resulting gases were then controlled to exact conditions of pressure, temperature and volume. Finally, the product gases were separated under steady-state conditions and are measured as a function of thermal conductivity. Using this analysis, the final material contained 2.94 wt % nitrogen.

About 77.5% of a solution derived from 1.27 g of rubidium acetate (Alfa Aesar, 99.8%, #12890) was dissolved in 2.5 g of water and was impregnated into 3 g of the material described above. The material was allowed to dry for at least 12 hours in a nitrogen environment. The material was loaded into an alumina boat and heated in a tube furnace. The internal diameter of the tube furnace was 10 cm. The airflow rate was greater than 1220 cm³/min, which corresponds to a linear velocity of greater than 15.6 cm/min. Use of this higher airflow is important to produce a high surface area material. The material was heated at a rate of 5° C./min to 120° C., and was exposed to this temperature for 4 hours. It was subsequently heated at a rate of 5° C./min to approximately 450° C. (as measured by a thermocouple placed approximately 0.5 cm over the catalyst bed) and was held at this temperature for 16 hours and allowed to cool to room temperature in air.

Catalyst 2 ($Al_1\ Si_x\ P\ (O_{(4+2x)-y})N_{2/3\ y}$, x=1, 115.88 g (0.86 moles) of aluminum trichloride (Alfa Aesar, 8848) was hydrolyzed with 322 g of water and left in solution overnight. One half of this hydrolyzed solution was used. 28.6 ml of 86% $H_3PO_4$ (JT Baker) was stirred into this half of the solution and was stirred well. 90 g (0.432 moles) of tetraethoxylsilane (TEOS) was added along with 100 ml of anhydrous ethanol.

After adding about 100 ml ammonium hydroxide (20–30%, EM Science) the material turned into a flaky white precipitate. An additional 25 ml of ammonium hydroxide was added to raise the pH. The material was dried for 48 hours under nitrogen.

75 g of this material was dispersed in 100 ml of water and was filtered under vacuum. The material was further washed with four aliquots of 50 ml of water and then with 50 ml of isopropyl alcohol. The material was dried under a nitrogen blanket for 12 hours.

The material was nitrided by placing the material in a tube furnace and heated in anhydrous ammonia. 10.01 g of the solid described above was loaded in an alumina boat, which was placed into a tube furnace and purged in $N_2$ for 12 hours (100 sccm $N_2$). The sample was heated to 500° C. in $N_2$ for 2 hours. The $N_2$ was replaced with 100 sccm anhydrous $NH_3$ and the powder was heated to 650° C., and allowed to soak at that temperature (in $NH_3$) for 5 hours. After switching the gas stream to 100 sccm $N_2$, the sample was allowed to slowly cool to room temperature.

LIQUID PHASE REACTION DATA

In the following examples, a 2 cc pressure vessel was charged with gamma-valerolactone (100 mg), paraformaldehyde (300 mg), toluene (700 mg, as a solvent) and catalyst (50 mg). Nitrogen was used to pressurize the vessel to 800 psi, which was then heated to 200° C. for 2 hours. The autoclave was then cooled, vented and the liquid analyzed by GC to determine conversion and selectivity.

| Catalyst | Time (hrs) | Temp (C.) | He Press (psi) | MeMBL Sel(%) | VL Con(%) |
|---|---|---|---|---|---|
| Catalyst 1 | 2 | 200 | 1000 | 15.79 | 4.15 |
| Comparative Catalyst 1 | 2 | 150 | 1000 | 2.74 | 7.67 |
| Catalyst 2 | 2 | 200 | 1000 | 13.85 | 4.50 |
| Comparative Catalyst 1 | 2 | 200 | 1000 | 1.27 | 15.28 |
| Catalyst 1 | 2 | 150 | 1000 | 5.06 | 11.65 |

This data shows that the present process provides the desired product with adequate conversions and selectivity.

The invention claimed is:

1. A process for preparing a reaction product comprising an alpha-methylene lactone of the Formula II, said process comprising reacting a lactone of the Formula I with formaldehyde

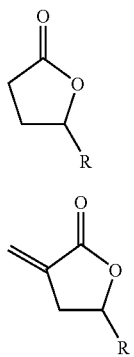

wherein R is selected from the group consisting of hydrogen, methyl, ethyl, and straight or branched $C_3$–$C_5$ alkyl;

at a temperature in the range of from about 100° C. to about 300° C. in the presence of an oxynitride catalyst of the nominal formula $Al_1\ Si_x\ P\ (O_{(4+2x)-y})\ N_{2/3\ y}$, wherein;

X=0 to 1, and
Y=0.001 to 2.

2. The process of claim 1 wherein the oxynitride catalyst is made by a process that comprises the steps of
  (a) combining $AlCl_3$ or alkoxides with water;
  (b) adding $H_3PO_4$ to the product of step (a);
  (c) optionally adding silicon alkoxide to the product of step (b);
  (d) adding $NH_4OH$ to the product of step (b), or to the product of step (c), if step (c) is performed;
  (e) drying the product of step (d);
  (f) optionally washing the product of step (e); and
  (g) heating the product of step (e) or (f) in $NH_3$.

3. A process for preparing a reaction product comprising an alpha-methylene lactone of the Formula II, said process comprising reacting a lactone of the Formula I with formaldehyde

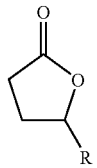

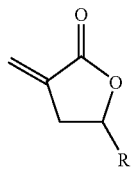

wherein R is selected from the group consisting of hydrogen, methyl, ethyl, and straight or branched $C_3$–$C_5$ alkyl;

at a temperature in the range of from about 100° C. to about 300° C. in the presence of a composite catalyst made by a process that comprises:
  (a) contacting (i) an oxynitride catalyst of the nominal formula $Al_1\ Si_x\ P\ (O_{(4+2x)-y})N_{2/3\ y}$ wherein;

X=0 to 1, and
  Y=0.001 to 2, with (ii) a solution comprising a solvent and a compound of at least one element selected from the group consisting of lithium, sodium, potassium, rubidium, cesium, magnesium, calcium, strontium and barium;
  (b) drying the product of step (a) to remove at least a portion of said solvent;
  (c) heating the product of step (b) to a temperature in the range of 350° C. to 550° C. to produce a catalyst precursor; and
  (d) flushing at a preselected flow rate an oxygen-containing gas over said catalyst precursor either during step (c), or after step (c) while the temperature is still in the range of 350° C. to 550° C. to produce the composite catalyst, in which the at least one element is present in said composite catalyst in an amount from about 0.1% to about 40% by weight of the combined weight of the oxynitride catalyst and the element.

4. The process of claim 3 wherein the oxynitride catalysts is made by a process that comprises the steps of:
  (a) combining $AlCl_3$ or alkoxides with water;
  (b) adding $H_3PO_4$ to the product of step (a);
  (c) optionally adding silicon alkoxide to the product of step (b);
  (d) adding $NH_4OH$ to the product of step (b), or to the product of step (c), if step (c) is performed;
  (e) drying the product of step (d);
  (f) optionally washing the product of step (e); and
  (g) heating the product of step (e) or (f) in $NH_3$.

5. The process of claim 1 wherein R is hydrogen or methyl.

* * * * *